United States Patent
Saito (10) Patent No.: US 9,204,791 B2
(45) Date of Patent: Dec. 8, 2015

(54) OCULAR OPTICAL SYSTEM

(75) Inventor: Kenichi Saito, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 103 days.

(21) Appl. No.: 13/639,268

(22) PCT Filed: Apr. 12, 2011

(86) PCT No.: PCT/JP2011/059476
§ 371 (c)(1),
(2), (4) Date: Oct. 4, 2012

(87) PCT Pub. No.: WO2011/129458
PCT Pub. Date: Oct. 20, 2011

(65) Prior Publication Data
US 2013/0021576 A1 Jan. 24, 2013

(30) Foreign Application Priority Data
Apr. 15, 2010 (JP) .................................. 2010-094119

(51) Int. Cl.
*A61B 3/12* (2006.01)
(52) U.S. Cl.
CPC ....................................... *A61B 3/12* (2013.01)
(58) Field of Classification Search
CPC ............ A61B 3/15; A61B 3/04; A61B 3/152; A61B 3/113; A61B 3/103; A61B 3/1225; A61B 3/1015; A61B 3/12; G01B 9/02; G06T 7/0012
USPC ......... 351/206, 208, 210, 211, 221, 233, 246; 356/479, 497, 498; 382/131
See application file for complete search history.

(56) References Cited

U.S. PATENT DOCUMENTS

| | | |
|---|---|---|
| 5,090,798 A | 2/1992 | Kohayakawa |
| 7,566,128 B2 | 7/2009 | Tsukada et al. |
| 2007/0070295 A1 | 3/2007 | Tsukada et al. |
| 2007/0159599 A1 | 7/2007 | Yamada |
| 2007/0291230 A1* | 12/2007 | Yamaguchi et al. .......... 351/221 |
| 2011/0242487 A1 | 10/2011 | Yuasa et al. |
| 2011/0249236 A1 | 10/2011 | Saito et al. |
| 2011/0279778 A1 | 11/2011 | Saito |
| 2011/0299034 A1* | 12/2011 | Walsh et al. .................. 351/206 |
| 2012/0274904 A1 | 11/2012 | Saito et al. |

FOREIGN PATENT DOCUMENTS

| | | |
|---|---|---|
| JP | 2007-117714 A | 5/2007 |
| WO | 2010/009450 A1 | 1/2010 |
| WO | WO 2010/009447 * | 1/2010 |

OTHER PUBLICATIONS

Jul. 14, 2011 International Search Report and Written Opinion in International Patent Appln. No. PCT/JP2011/059476.
B. Hermann, et al., "Adaptive-optics ultrahigh-resolution optical coherence tomography", Optics Letters, vol. 29, No. 18, Sep. 15, 2004, pp. 2142-2144.
Oct. 16, 2012 International Preliminary Report on Patentability in International Patent Appln. No. PCT/JP2011/059476.

* cited by examiner

*Primary Examiner* — Thomas K Pham
*Assistant Examiner* — Jie Lei
(74) *Attorney, Agent, or Firm* — Fitzpatrick, Cella, Harper & Scinto (57) ABSTRACT

Provided is an ocular optical system, which permits a measuring beam scanned by two scanning units disposed close to each other to enter an anterior ocular segment of an eye to be inspected and to irradiate a fundus. The ocular optical system includes an optical unit which is disposed at a position of an intermediate image, which is optically conjugate to the fundus, and has a surface having different optical powers corresponding to scan directions of the two scanning units.

31 Claims, 10 Drawing Sheets

OCULAR OPTICAL SYSTEM

TECHNICAL FIELD

The present invention relates to an ocular optical system, and particularly to an ocular optical system of an apparatus for taking an image of an eye retina.

BACKGROUND ART

As an ophthalmologic apparatus for examining an eye retina, there is known a scanning laser ophthalmoscope (SLO) which obtains a two-dimensional image of a retina as a plane. In addition, there is also known an optical coherence tomography (OCT) which obtains a tomographic image of a retina in a noninvasive manner. Those apparatuses have been put into practical use for a long time. Those apparatuses scan a retina by a light beam in a two-dimensional manner using a deflector, and synchronously measure reflected and backscattering light so as to obtain a two-dimensional image or a three-dimensional image of the retina.

Spatial resolution of the obtained image in a plane direction (lateral direction) of the retina (hereinafter, referred to as lateral resolution) is determined basically by a spot diameter of the beam that scans the retina. In order to reduce the spot diameter of the beam condensed on the retina, only the diameter of the beam that enters the eye needs to be increased. However, curved surface shapes and refractive index homogeneity of cornea and lens that perform the refracting action in an eyeball are not complete, which causes high order aberration in a wavefront of the transmitted light. Therefore, even if a thick beam enters, the spot on the retina cannot be condensed to a desired diameter and, on the contrary, is expanded. As a result, the lateral resolution of the obtained image is decreased, and the S/N ratio of the obtained image signal is also decreased. Therefore, conventionally, it has been common to use incident light of a thin beam of approximately 1 mm diameter that is hardly affected by aberration of the eye's optical system, and to form a spot of approximately 20 μm diameter on the retina.

A structure that is generally and often used in the two-dimensional scan optical system such as SLO or OCT is the structure in which two one-dimensional scanner mirrors are disposed close to each other (hereinafter, referred to as a tandem type). PTL 1 discloses a structure in which galvano mirrors, each of which can rotate about a rotation axis, are disposed close to each other so that the rotation axes are perpendicular to each other, and the incident beam is deflected in the two-dimensional direction so as to enter the pupil of the eyeball via an imaging optical system and an objective lens. In addition, NPL 1 discloses a structure using a two-dimensional scanner having a similar structure, in which a thick beam of 3.68 mm diameter is formed as the incident beam of the eyeball, and a compensation optical system using a wavefront sensor and a variable shape mirror is also disposed for correcting influence of aberration of the eyeball optical system.

CITATION LIST

Patent Literature

PTL 1: Japanese Patent Application Laid-Open No. 2007-117714

Non Patent Literature

NPL 1: B. Hermann et al., "Adaptive-optics ultrahigh-resolution optical coherence tomography", OPTICS LETTERS, Vol. 29, No. 18, Sep. 15, 2004

SUMMARY OF INVENTION

Technical Problem

When the two scanning units are disposed close to each other, if one of the two scanning units is disposed at a position conjugate to the anterior ocular segment, another scanning unit is not disposed at the position conjugate to the anterior ocular segment. Therefore, the incident position of the measuring beam scanned by the another scanning unit in the anterior ocular segment may have a large deviation. In this case, for example, a light amount loss occurs due to vignetting generated by the iris, which is not preferred.

Solution to Problem

In order to solve the above-mentioned problem, the present invention provides an ocular optical system, which permits a measuring beam scanned by two scanning units disposed close to each other to enter an anterior ocular segment of an eye to be inspected and to irradiate a fundus, in which the optical system includes an optical unit which is disposed at a position of an intermediate image, which is optically conjugate to the fundus, and has a surface having different optical powers corresponding to scan directions of the two scanning units.

Advantageous Effects of Invention

According to the present invention, an optical unit is provided which is disposed at a position of an intermediate image, which is optically conjugate to the fundus, and has a surface having different optical powers corresponding to scan directions of the two scanning units. Thus, it is possible to reduce the deviation of the incident position of the measuring beam in the anterior ocular segment due to that one of two scanning units disposed close to each other is disposed at a position conjugate to the anterior ocular segment while another scanning unit is not located at the position conjugate to the anterior ocular segment.

Further features of the present invention will become apparent from the following description of exemplary embodiments with reference to the attached drawings.

DESCRIPTION OF EMBODIMENTS

Preferred embodiments of the present invention will now be described in detail in accordance with the accompanying drawings.

Figure 3:
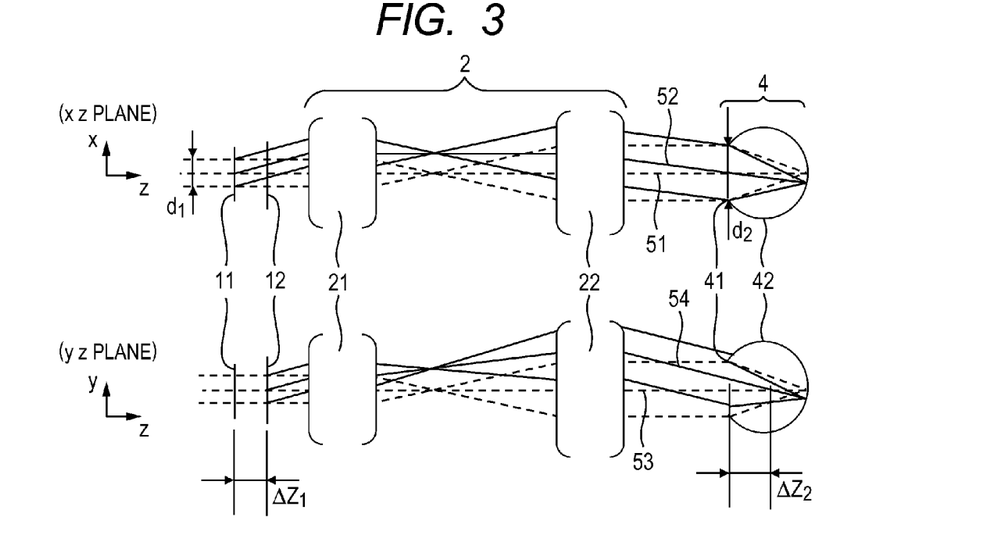
FIG. 3 is a structural diagram of a conventional ocular optical system.

Hereinafter, a reason why a deviation occurs in the incident position of the measuring beam in the anterior ocular segment is described in detail. In recent years, a technology for compensation optics, which compensates for even high order wavefront aberration using an active optical element, is in the actual use and is being applied also to fundus measurement. In this technology, wavefront aberration generated due to characteristics of the subject itself or variation of measurement environment is measured sequentially by a wavefront detector, and is compensated by a wavefront aberration compensator such as a variable shape mirror or a space optical modulator. An example is reported in which a thick beam of approximately 7 mm diameter is introduced into an eyeball using the above-mentioned technology, and is condensed to approximately 3 μm diameter that is close to a diffraction limitation on a retina by wavefront compensation, with the result that an SLO image or an OCT image having high resolution is obtained. When a thick incident beam is formed in this way, there is a point to be noted in view of a structure of the optical system. The point is described with reference to FIG. 3 in which an ocular optical system using the tandem type two-dimensional scanner is developed linearly. In this structure, at least a few millimeters of a distance $\Delta Z_1$ is necessary between rotational axes of a scanner 11 for horizontal scan (hereinafter, referred to as x scanner) and a scanner 12 for vertical scan (hereinafter, referred to as y scanner). Therefore, at least one of the scanners is not optically conjugate to an eyeball pupil 41. In FIG. 3, the x scanner 11 is conjugate to the eyeball pupil 41, but an image of the y scanner 12 is shifted by $\Delta Z_2$ from the pupil 41 to the inside of the eyeball. Here, the sentence "the two objects are conjugate" means that the two object have a positional relationship between an object point and an image point.

If a pupil incident beam diameter $d_2$ is approximately 1 mm, it is easy to set a pupil magnification (lateral magnification) β of an ocular optical system 2, which is a ratio of the pupil incident beam diameter $d_2$ to a scanner incident beam diameter $d_1$, to a value smaller than one as a reduction system. Therefore, the pupil position shift amount $\Delta Z_2$ can be reduced to a negligibly small value. For example, when the scanner incident beam diameter $d_1$ is 4 mm, and the pupil incident beam diameter $d_2$ is 1 mm, the lateral magnification β is $d_2/d_1$=0.25. Therefore, a longitudinal magnification $\alpha=\beta^2$ is 0.0625. In this case, even if the distance $\Delta Z_1$ between scanner rotational axes is 10 mm, the pupil position shift amount $\Delta Z_2$ can be reduced to 0.625 mm. If the beam diameter is 4 mm, it is sufficient that the scanner mirror diameter be approximately 6 mm to 7 mm. The scanner that satisfies the necessary mirror diameter, deflection angle, and drive frequency can be easily obtained.

On the other hand, in order to thicken the pupil incident beam diameter $d_2$ in the above-mentioned ocular optical system 2, the lateral magnification β needs to be increased, or the scanner incident beam diameter $d_1$ needs to be increased. However, if the lateral magnification is increased to satisfy β>1 as in the former method, the pupil position shift amount $\Delta Z_2$ is increased. If $d_1$=4 mm and $d_2$=6 mm are satisfied, α is $(6/4)^2$=2.25 so that the pupil position shift amount $\Delta Z_2$ becomes as large as 20 mm or larger (here, refractive power of the anterior ocular segment is not taken into account for simple description). When $\Delta Z_2$ is increased as described above, firstly an off-axis light beam is vignetted by the iris so that a desired spot diameter cannot be formed on the retina. As a result, amounts of light projected to the retina, and reflected and backscattering light from the retina are all decreased. In addition, a distortion may occur in the scanned area on the retina, so that image quality is deteriorated.

Further, when the compensation optics is used, it is necessary that the pupil of the eyeball, the wavefront sensor, and the wavefront compensator be optically conjugate. However, in the example illustrated in FIG. 3, the conjugate relationship is not satisfied in a yz plane. Therefore, there is a problem that correct wavefront measurement and correction cannot be performed.

In addition, even if the scanner incident beam diameter $d_1$ is increased as in the latter method, $d_1$ needs to be enormously increased as the reduction optical system. As a result, the scanner mirror is also increased so that the scanner interval $d_1$ needs to be also increased. Finally, it is very difficult to set the pupil position shift amount $\Delta Z_2$ to a value smaller than 1 mm.

Figure 4:
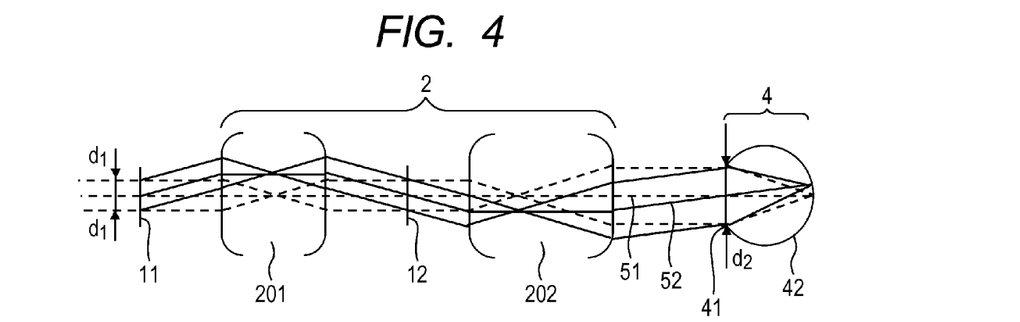
FIG. 4 is a structural diagram of a conventional ocular optical system.

In order not to generate such a pupil position shift amount $\Delta Z_2$, it is considered to adopt a structure of the ocular optical system 2 in which a relay optical system 201 is disposed between the scanners as illustrated in FIG. 4. Thus, both the x scanner 11 and the y scanner 12 can be disposed at positions conjugate to the pupil 41, but a size of the optical system is increased, and both cost of components and man-hour for adjustment are increased. In addition, efficiency of the optical system is decreased, and the S/N ratio of the image is also decreased. If the two-dimensional scanner is of a type in which one mirror rotates in two axis directions, the pupil position shift amount is not generated without using the relay optical system. However, it is currently difficult to obtain the scanner satisfying the necessary performance. Therefore, an ocular optical system according to the present invention includes an optical unit which is disposed at an intermediate image position that is optically conjugate to the fundus and has a surface having different optical powers corresponding to scan directions of the two scanning units. Thus, it is possible to reduce the deviation of the incident position of the measuring beam in the anterior ocular segment (pupil position shift amount), which occurs because one of two scanning units disposed close to each other is disposed at a position conjugate to the anterior ocular segment while another scanning unit is not located at the position conjugate to the anterior ocular segment.

Hereinafter, the ocular optical system according to the present invention is described based on embodiments with reference to the drawings.

First Embodiment

Figure 1:
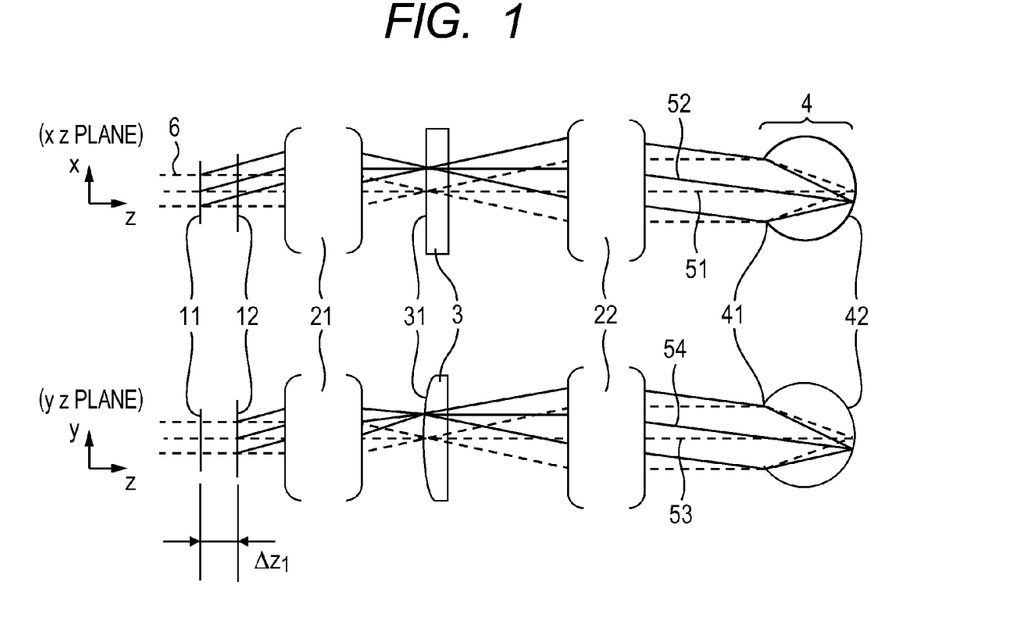
FIG. 1 is a cross section of an ocular optical system according to a first embodiment of the present invention.

FIG. 1 illustrates a cross section of an ocular optical system according to this embodiment. A beam 6 that is emitted from a light source (not shown) and is collimated is deflected in two-dimensional direction by two one-dimensional scanner mirrors 11 and 12 (corresponding to one-dimensional beam scanning units in the embodiments) disposed close to each other, and is led to an iris 41 of an eyeball 4 by an ocular optical system 2. Here, the sentence "two one-dimensional scanners 11 and 12 are disposed close to each other" in this embodiment means that the two one-dimensional scanners 11 and 12 are disposed close to each other without operational interference therebetween. The sentence also includes the case where there is no optical element having an optical power between the two one-dimensional scanners 11 and 12, and the two one-dimensional scanners 11 and 12 are disposed at such a distance that the shift amount described above can be compensated by a cylindrical lens that is described later. Note that, the optical path including a reflection path of the scanner mirror is illustrated here as a linear path for easy view. In addition, the eyeball is supposed to have an ideal lens with zero diopter scale and no aberration for simple description. The collimated beam entering the iris 41 is condensed on a retina 42 by an anterior optical system such as a cornea (not shown). Here, the horizontal direction is denoted by x and the vertical direction is denoted by y, and cross sections of an xz plane and the yz plane are illustrated. It is supposed that the beam is scanned by the scanner 11 in an x direction and is scanned by the scanner 12 in a y direction. In other words, the beam 6 as the measuring beam enters the anterior ocular segment of an eye to be inspected so as to irradiate and scan the fundus by the two scanning units disposed close to each other.

A pupil magnification β of this ocular optical system is two times. When the diameter of the beam 6 entering the x scanner mirror 11 is 3 mm, the diameter of the beam entering the iris 41 is 6 mm. Therefore, when the focal length of the eyeball optical system is 22 mm and the wavelength of the beam is 850 nm, a beam spot diameter on the retina 42 is approximately 4 µm.

The ocular optical system includes a lens unit 21 having a focal length of $f_1$ (>0) (corresponding to a first optical element in the embodiments) and a lens unit 22 having a focal length of $f_2$ (>0), which have a relationship satisfying $f_2=2 \cdot f_1$. In this case, the x scanner mirror 11 and the eyeball pupil 41 are disposed at positions that are optically conjugate by the ocular optical system 2. When the beam 6 deflected by the x scanner mirror 11 enters the eyeball 4 at a field angle, a principal light beam 52 thereof passes through the center of the eyeball pupil 41.

At the same time, the ocular optical system includes a cylindrical lens 3 (corresponding to a second optical element in the embodiments) disposed in a vicinity of an intermediate image position that is optically conjugate to the retina, between the lens units 21 and 22. Here, the "intermediate image position" is a position on the optical axis of the ocular optical system. This cylindrical lens 3 is disposed so as to have a refractive power only in a yz cross sectional direction and no refractive power in an xz cross sectional direction. In this case, it is supposed that there is a beam scanned in the y direction in the yz cross section. Here, a cylindrical surface 31 of the cylindrical lens 3 is set so as to agree substantially with the intermediate image position, namely the position where the beam is condensed. Thus, the beam scanned by the cylindrical surface 31 so as to pass off the optical axis (as illustrated in FIG. 1 by solid lines) is bent, but the wavefront of the beam is hardly affected. In other words, the cylindrical lens has the function as a so-called field lens only in the yz cross sectional direction. Therefore, when a curvature of the cylindrical surface, namely a focal length of the cylindrical lens, is selected appropriately, it is possible that a principal light beam 54 is set to finally pass through the center of the eyeball pupil 41, and it is possible that the collimation degree of the beam entering the pupil can be maintained so that no defocusing occurs.

Figure 12:
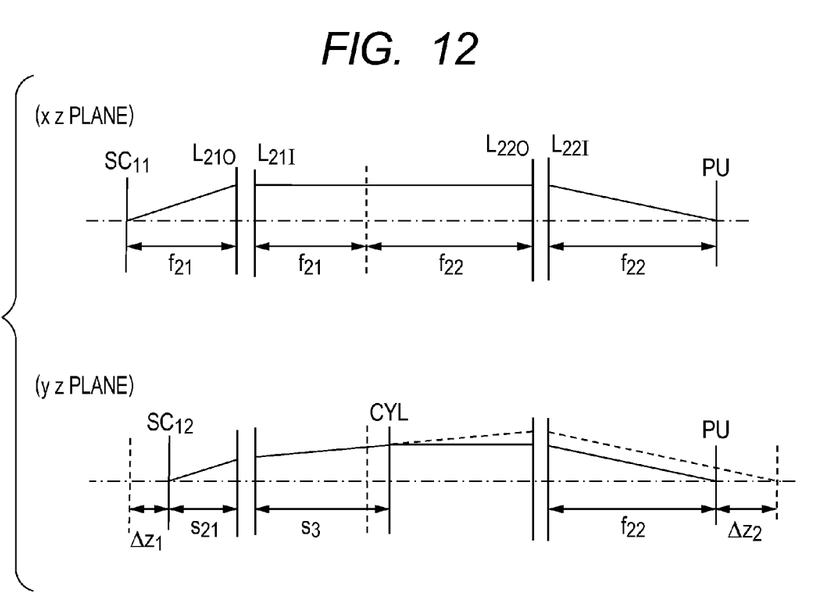
FIG. 12 is a diagram illustrating a lens arrangement and a principle of calculating a focal length.

In order to set a value of $\Delta Z_2$ to zero, the cylindrical surface 31 only needs to substantially agree with the intermediate image position. A relationship between the position where the cylindrical lens is disposed and the focal length of the cylindrical lens for satisfying the above-mentioned relationship is described with reference to FIG. 12 and equations. Here, based on the structure illustrated in FIG. 1, in the xz cross section, it is supposed that there is an optically conjugate positional relationship between an x scanner mirror reference point $SC_{11}$ and an eyeball pupil PU when the lens unit 21 having a focal length of $f_{21}$ and the lens unit 22 having a focal length of $f_{22}$ are disposed as illustrated in FIG. 12. Here, the lens unit 21 has a principal point position $L_{21O}$ on the scanner side and a principal point position $L_{21I}$ on the eyeball pupil side, while the lens unit 22 has a principal point position $L_{22O}$ on the scanner side and a principal point position $L_{22I}$ on the eyeball pupil side. In addition, it is supposed that the x scanner mirror reference point $SC_{11}$ is a beam incident position to the x scanner mirror (rotational axis position on mirror surface). As for the yz cross section too, according to the structure illustrated in FIG. 1, the cylindrical lens is disposed so that a principal point CYL on the scanner side is positioned at a distance $s_3$ from $L_{21I}$. In this case, if CYL has no optical power, a conjugate position of a y scanner mirror reference point $SC_{12}$ disposed at a position distant from the x scanner mirror reference point $SC_{11}$ by $\Delta z_1$ is shifted from the eyeball pupil PU by $\Delta z_2$ as indicated in the yz cross section. Here, the y scanner mirror reference point $SC_{12}$ is a beam incident position to the y scanner mirror (rotational axis position on the mirror surface) when the beam passes along the optical axis of the ocular optical system. In order to set the value of $z_2$ to 0, the position $s_3$ of the principal point CYL of the cylindrical lens on the scanner side and a focal length of $f_{CYL}$ are determined based on a paraxial imaging formula as follows.

Here in the yz cross section, the object point of the lens unit 21 is the y scanner reference point $SC_{12}$, and a distance between the y scanner reference point $SC_{12}$ and the scanner side principal point $L_{21O}$ is $s_{21}$ ($=-(f_{21}-\Delta z_1)<0$). Here, the sign is positive in the direction from the scanner to the eyeball pupil side. Therefore, the distance between the principal point $L_{21I}$ on the eyeball pupil side and the image point position of the lens unit 21 in this case is $S_{22}$, which satisfies the equation below.

$$1/s_{22}=1/s_{21}+1/f_{21} \quad \text{(equation 1)}$$

Here, when the CYL is disposed at a distance of $-s_3$ ($s_3<0$) from the principal point $L_{21I}$ on the eyeball pupil side of the lens unit 21, in the same manner, the position of the image point of the CYL is $S_{32}$, in which the distance from the CYL satisfies the equation below.

$$1/s_{32}=1/(s_{22}+s_3)+1/f_{CYL}=1/[1/\{1/s_{21}+1/f_{21}\}+s_3]+1/f_{CYL} \quad \text{(equation 2)}$$

In order that the image point of the lens unit 22 finally agrees with the same position as the image point in the xz cross section, namely the point at a distance of $f_{22}$ from the principal point position $L_{22I}$ on the eyeball pupil side of the lens unit 22, $s_{32}=\infty$ only needs to be satisfied. Therefore, a value of $f_{CYL}$ only needs to be selected so that the right side of the equation given above becomes zero. Therefore, the following equation holds.

$$f_{CYL}=-1/\{1/s_{21}+1/f_{21}\}-s_3 \quad \text{(equation 3)}$$

According to this equation (3), supposing $f_{21}=50$ (mm), $f_{22}=100$ (mm), $\Delta z_1=10$ (mm), and $s_3=-50$ (mm), for example, $f_{CYL}$ only needs to be set to 250 mm. Further, if each of the optical elements is a mirror, it is supposed that the principal points on the scanner side and on the eyeball pupil side agree with each other.

In order to set a value of $\Delta Z_2$ to zero, the cylindrical surface 31 only needs to substantially agree with the intermediate image position. In order to prevent deterioration of the beam or decrease in light amount due to a flaw or dust on the surface of the lens, the cylindrical surface 31 and the intermediate image position may be separated from each other in such a range that astigmatism is not generated conspicuously. In this case, it is desirable that the cylindrical surface be closer to the intermediate image position than any other surface having optical power.

As described above, it is possible to reduce the pupil position shift amount $\Delta Z_2$ that is generated in the structure illustrated in FIG. 3 to a negligible amount without using the relay optical system 201 illustrated in FIG. 4. The cylindrical lens is used here as an element having different optical powers in the xz cross section and in the yz cross section, but an anamorphic lens or the like may be used. In other words, in the present invention, an anamorphic lens or the like as the optical unit only needs to be used, which has a surface having different optical powers corresponding to scan directions of the x scanner 11 and the y scanner 12 as the two scanning units, and the optical unit only needs to be disposed at the intermediate image position that is optically conjugate to the fundus.

Figure 2:
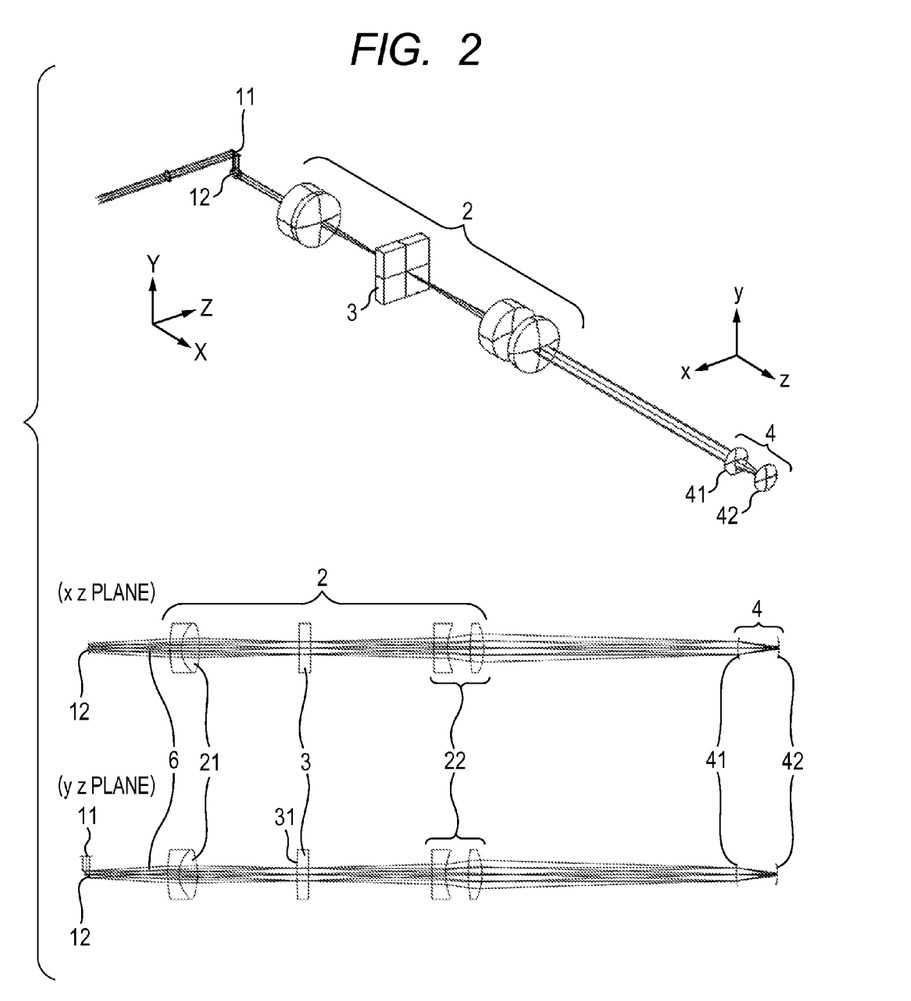
FIG. 2 is a structural diagram of the ocular optical system according to the first embodiment of the present invention.

A specific example to which this fundamental structure of the ocular optical system is applied is illustrated in FIG. 2. Here, it is supposed that the ocular system is applied to a retina projection type image display apparatus. The upper part of FIG. 2 illustrates a bird's eye view of the ocular optical system and the lower part illustrates an xz cross section and a yz cross section. In this embodiment, the entire ocular optical system is constituted of lens elements as illustrated in FIG. 1, and the individual parts are denoted by the same numerals as those in FIG. 1. The viewer's eyeball 4 is illustrated only with the cornea surface 41 and the retina surface 42 for easy view. Note that, the eyeball 4 is also referred to as an eye to be inspected in the present invention.

The collimated beam 6 formed by a light source and a collimator lens (not shown) is scanned by the x scanner 11 and the y scanner 12 in a two-dimensional manner, and is led to the viewer's eyeball 4 by the ocular optical system. Here, a distance between both scanners is set to 8 mm, and a diameter of the incident beam is set to 3 mm. The lateral magnification β of the ocular optical system is two times. The scan angle of the scanner mirror is 3.4 degrees in each scan direction. Therefore, the scan angle on the scanner side is 6.8 degrees, and the scan angle on the eyeball pupil side is 3.4 degrees in each scan direction. As a result, an area of 1.07 mm×1.07 mm on the retina 42 is scanned. In addition, the diameter of the beam entering the eyeball pupil 41 is 6 mm, and the spot diameter on the retina 42 is approximately 4 μm. Note that, the eyeball is assumed as an ideal lens here, too. With this structure, when the light source is modulated in synchronization with the scanning by the scan mirrors, the viewer can recognize a two-dimensional image.

Figure 8:
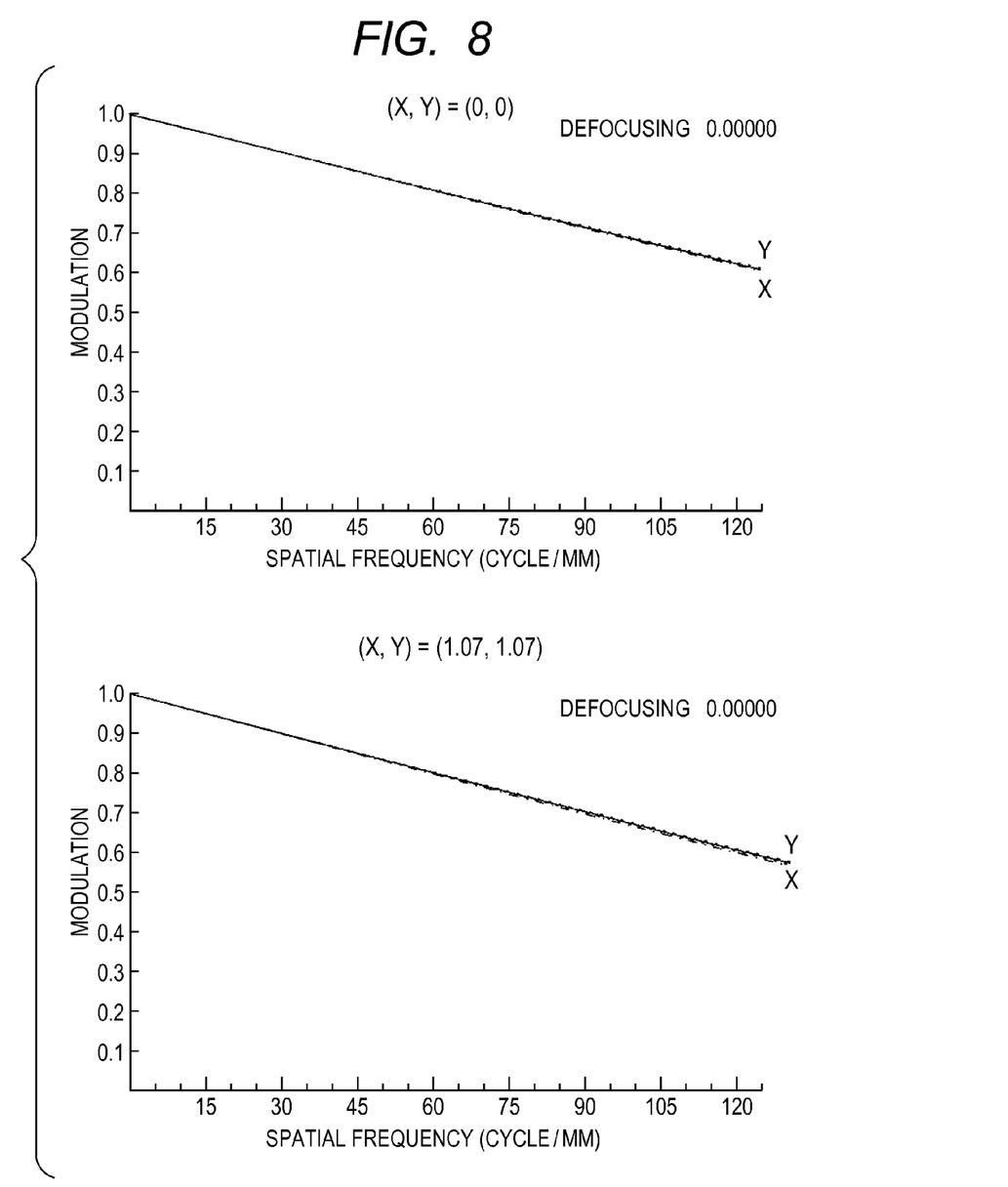
FIG. 8 is MTF diagrams of the optical system according to the first embodiment of the present invention.

Here, a focal length f of the cylindrical lens 3 (at wavelength of 587.56 nm) is set to 308.76 mm. As a result, the pupil position shift amount $\Delta Z_2$ in the maximum scan angle beam is reduced to approximately 0.2 mm, with the result that the pupil is formed appropriately in each cross section illustrated in FIG. 2. In addition, simultaneously, as to image performance of the optical system including the eyeball, as understood from graphs of the modulation transfer function (MTF) of the beam on the optical axis and the maximum scan angle beam illustrated in FIG. 8, both beams maintain good values substantially close to the diffraction limitation.

Hereinafter, lens data of this embodiment is shown. Here, X, Y, and Z are respectively different from coordinates x, y, and z on the retina that are coordinates with respect to the coordinates of the aperture stop position as the origin. The unit of the positions in X, Y, and Z directions is millimeters, and the unit of a rotation angle in each axis is degrees in the counterclockwise direction. Here, the surface closest to the intermediate image position is the flat surface of the cylindrical lens that has no optical power, and the cylindrical surface 31 is disposed at the position closer to the intermediate image position than any other surface having optical power.

| Surface No. | Radius curvature | X position | Y position | Z position | Rotational axis X | Rotational axis Y | Glass |
|---|---|---|---|---|---|---|---|
| Stop | ∞ | 0.000 | 0.000 | 0.000 | 0.000 | 0.000 | Air |
| 2 | ∞ | 0.000 | 0.000 | 30.000 | 45.000 | 0.000 | (Reflection) |
| 3 | ∞ | 0.000 | 0.000 | 30.000 | 90.000 | 0.000 | Air |
| 4 | ∞ | 0.000 | −8.000 | 30.000 | 90.000 | 45.000 | (Reflection) |
| 5 | ∞ | 0.000 | −8.000 | 30.000 | 0.000 | 90.000 | Air |
| 6 | ∞ | 0.000 | −8.000 | 30.000 | 0.000 | 90.000 | Air |
| 7 | 138.973 | −46.656 | −8.000 | 30.000 | 0.000 | 90.000 | STIH4_OHARA |
| 8 | 15.000 | −51.656 | −8.000 | 30.000 | 0.000 | 90.000 | SBAM4_OHARA |
| 9 | −24.554 | −59.656 | −8.000 | 30.000 | 0.000 | 90.000 | Air |
| 10 | 233.175 | −104.379 | −8.000 | 30.000 | 0.000 | 90.000 | STIH4_OHARA (CYL) |
| 11 | ∞ | −109.379 | −8.000 | 30.000 | 0.000 | 90.000 | Air |
| 12 | −267.271 | −173.836 | −8.000 | 30.000 | 0.000 | 90.000 | STIH10_OHARA |
| 13 | 29.805 | −179.836 | −8.000 | 30.000 | 0.000 | 90.000 | Air |
| 14 | 79.482 | −188.012 | −8.000 | 30.000 | 0.000 | 90.000 | SBAL50_OHARA |
| 15 | −25.252 | −194.012 | −8.000 | 30.000 | 0.000 | 90.000 | Air |
| 16 | ∞ | −269.4289 | −8.000 | 30.000 | 0.000 | 90.000 | (Eyeball incident surface) |

Second Embodiment

Next, a second embodiment is described below in the case where a scan type retinal inspection instrument is supposed, which measures reflection light from the retina. In the case of the structure illustrated in FIG. 2, the cylindrical surface 31 has a relationship nearly optically conjugate to the retina 42. When the beam 6 passes along the optical axis, the reflection light from this cylindrical surface 31 is also detected. The reflectance of the retina is approximately $10^{-3}$%. Therefore, the reflected and the backscattering light is very weak while the reflectance of the lens surface is actually a little lower than 0.1% even if an antireflection coating is formed. Therefore, the intensity of undesired reflection light from the lens is much higher. Therefore, when the beam is scanned in a two-dimensional manner so as to form an image, the undesired reflection light causes a strong ghost image to be a serious image failure.

Figure 5:
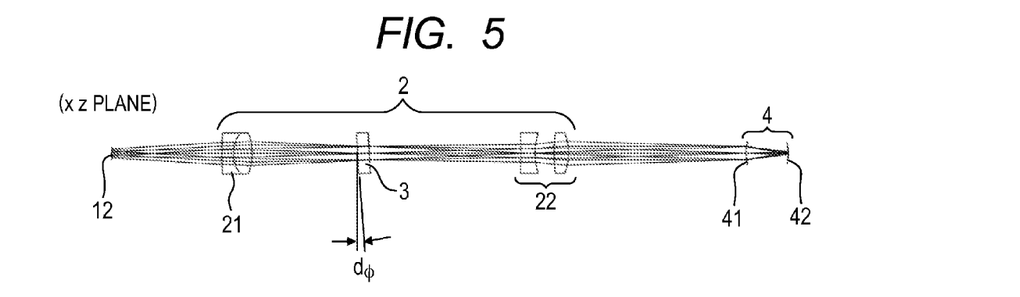
FIG. 5 is a structural diagram of an ocular optical system according to a second embodiment of the present invention.

Therefore, in this embodiment, as illustrated in FIG. 5, the cylindrical lens 3 is inclined with respect to the optical axis of the ocular optical system so that the reflection light from the cylindrical surface 31 is not detected. The individual lenses 21, 22, and 3, and distances between lenses in this embodiment are the same as those in the first embodiment, but the cylindrical lens 3 is inclined by dφ degrees with respect to the axis perpendicular to the generatrix of the cylindrical surface (here, y axis). Thus, it is possible to prevent the reflection light from the surface of the cylindrical lens 3 from being detected. Here, it is supposed that the ocular optical system of this embodiment is applied to the SLO, for example, and description is given based on FIG. 6 that illustrates the structure up to the cylindrical lens 3 in an SLO confocal optical system.

Figure 6:
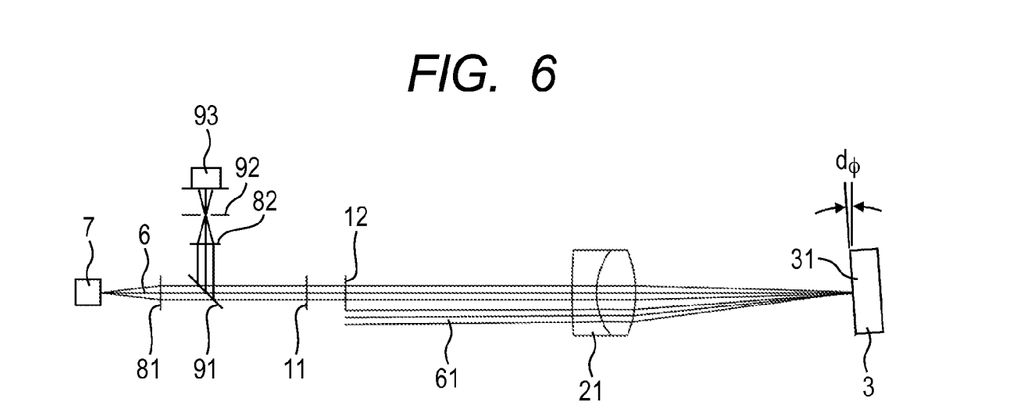
FIG. 6 is a diagram illustrating an effect of the second embodiment of the present invention.

The diverging beam 6 emitted from a light source 7 is collimated by a collimator lens 81 and reaches the cylindrical lens 3 via the x scanner 11, the y scanner 12, and the positive power lens 21. After that, the beam is led to the eyeball via a lens (not shown). The beam is condensed to the retina and is reflected, and then passes along the opposite optical path. After that, a part of the beam is reflected by an optical branching member 91 and is led to a light receiving sensor 93 via a lens 82 and a pinhole 92. Here, the retina and the pinhole 92 have a positional relationship optically conjugate to each other, so as to detect only the reflected and backscattering light from a very small point on the retina corresponding to the diameter of the pinhole 92. Note that, the optical path including the path folded by the scanner mirror is illustrated like a straight line for easy view.

Figure 9:
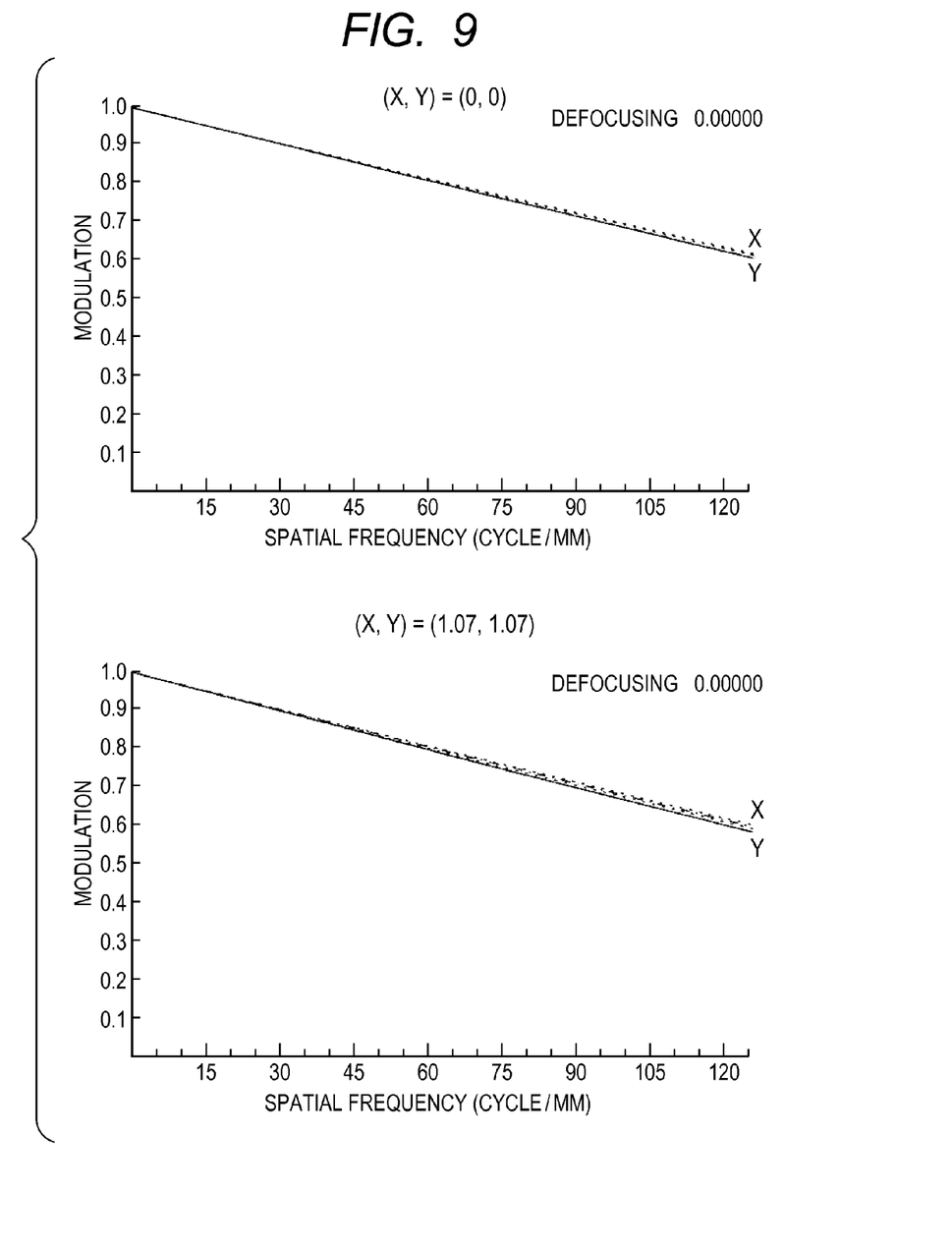
FIG. 9 is MTF diagrams of the optical system according to the second embodiment of the present invention.

In the structure illustrated in FIG. 2, the reflection light from the surface of the cylindrical lens 3 is also detected after passing through the pinhole 92 as described above. However, when the inclination dφ of the cylindrical lens 3 is 3 degrees, for example, reflection light 61 from the cylindrical surface 31 passes along an optical path different from the optical path of the incident light 6 and does not enter the y scanner 12. Therefore, the reflection light 61 does not reach the pinhole 92. Therefore, it is possible to obtain a good image from which the reflection light from the surface 31 is eliminated. In addition, deterioration of aberration due to the inclination of the cylindrical lens 3 is negligible in level, and the image performance thereof is almost the same as the case without inclination as illustrated in FIG. 9 so that the quality close to the diffraction limitation is maintained. However, the optical axes of the lens unit 22 and the eyeball 4 are shifted in the opposite directions by the same amount so as to cancel the optical axis shift generated by inclining the cylindrical lens 3.

In this embodiment, the cylindrical lens 3 is inclined in the direction with respect to the rotational axis that is the axis perpendicular to the generatrix of the cylindrical surface. However, the cylindrical lens 3 may be inclined with respect to the generatrix as the rotational axis. However, because the inclination of the normal of the reflection surface becomes small, the separation amount of the eliminated reflection ghost light is decreased so that the effect is also decreased.

Third Embodiment

Figure 7:
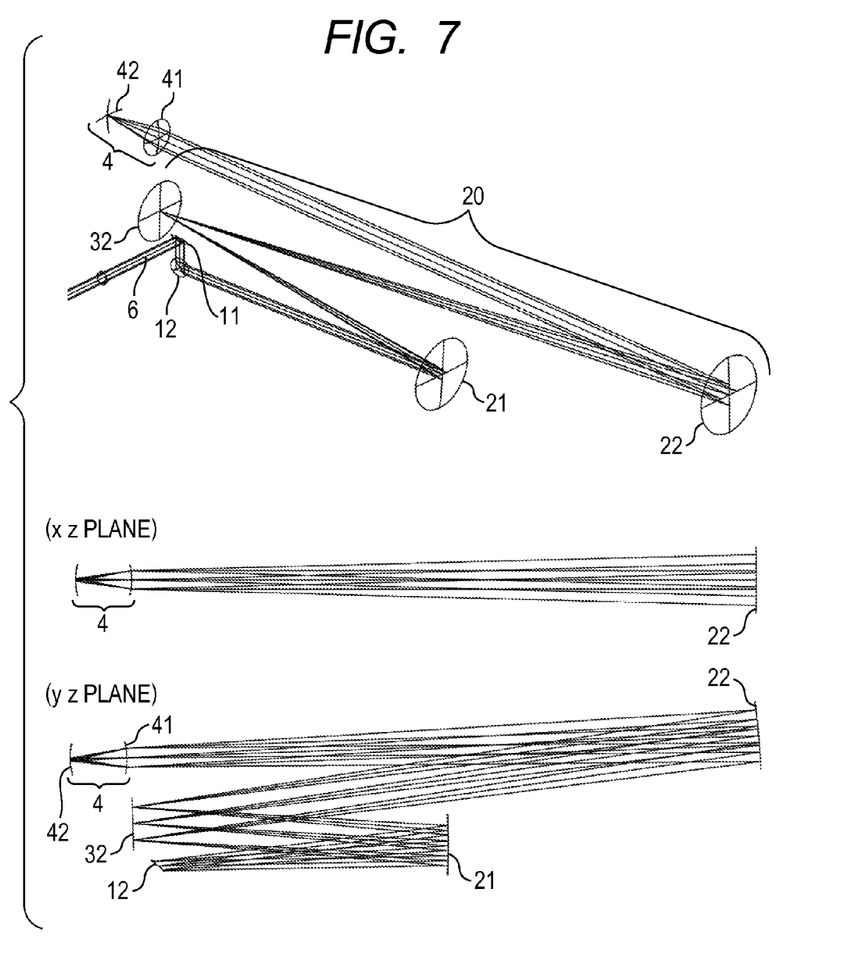
FIG. 7 is a structural diagram of an ocular optical system according to a third embodiment of the present invention.

A third embodiment is described with reference to FIG. 7. As described above, when a thick beam enters so as to form a spot diameter that is as small as a few microns on the retina, the spot is disturbed by aberration of the eyeball optical system so that a desired condensing state cannot be obtained. Therefore, it is necessary to use a compensation optical system. In this case, it is well known that an inconvenience occurs in a transparent type coaxial optical system using lenses in the type where the light irradiating the retina for obtaining an image is also used as irradiation light for measuring the wavefront. This is because that in the case where a Shack-Hartmann type wavefront sensor is used as the wavefront detector, for example, not only the reflected and backscattering light from the retina but also reflection light from each lens surface enter the wavefront sensor as undesired light. As described above, the reflection light from the lens surface has much larger intensity than that of the reflected and backscattering light from the retina. Therefore, it becomes difficult to measure the wavefront correctly. For this reason, the OCT or SLO optical system using the compensation optical system is constituted of an eccentric reflection system in many cases. In this embodiment, the case where the structure of the present invention is applied to the reflection optical system is described.

The beam 6 formed by a light source and a collimator lens (not shown) is first deflected by the x scanner 11 and the y scanner 12 in a two-dimensional manner. After that, the beam 6 is led to the eyeball 4 via the ocular optical system constituted of a spherical mirror 21 having positive power, a cylindrical mirror 32 having positive power, and a spherical mirror 22 having positive power. Here, the incident beam diameter to the x scanner 11 is 3 mm, the lateral magnification of the ocular optical system is two times, and the incident beam diameter to the eyeball is 6 mm. The spot diameter on the retina is approximately 4 μm. Note that, the xz cross section is illustrated from the spherical mirror 22 to the eyeball, and the yz cross section is illustrated from the y scanner 12 to the eyeball, for easy view.

Figure 10:
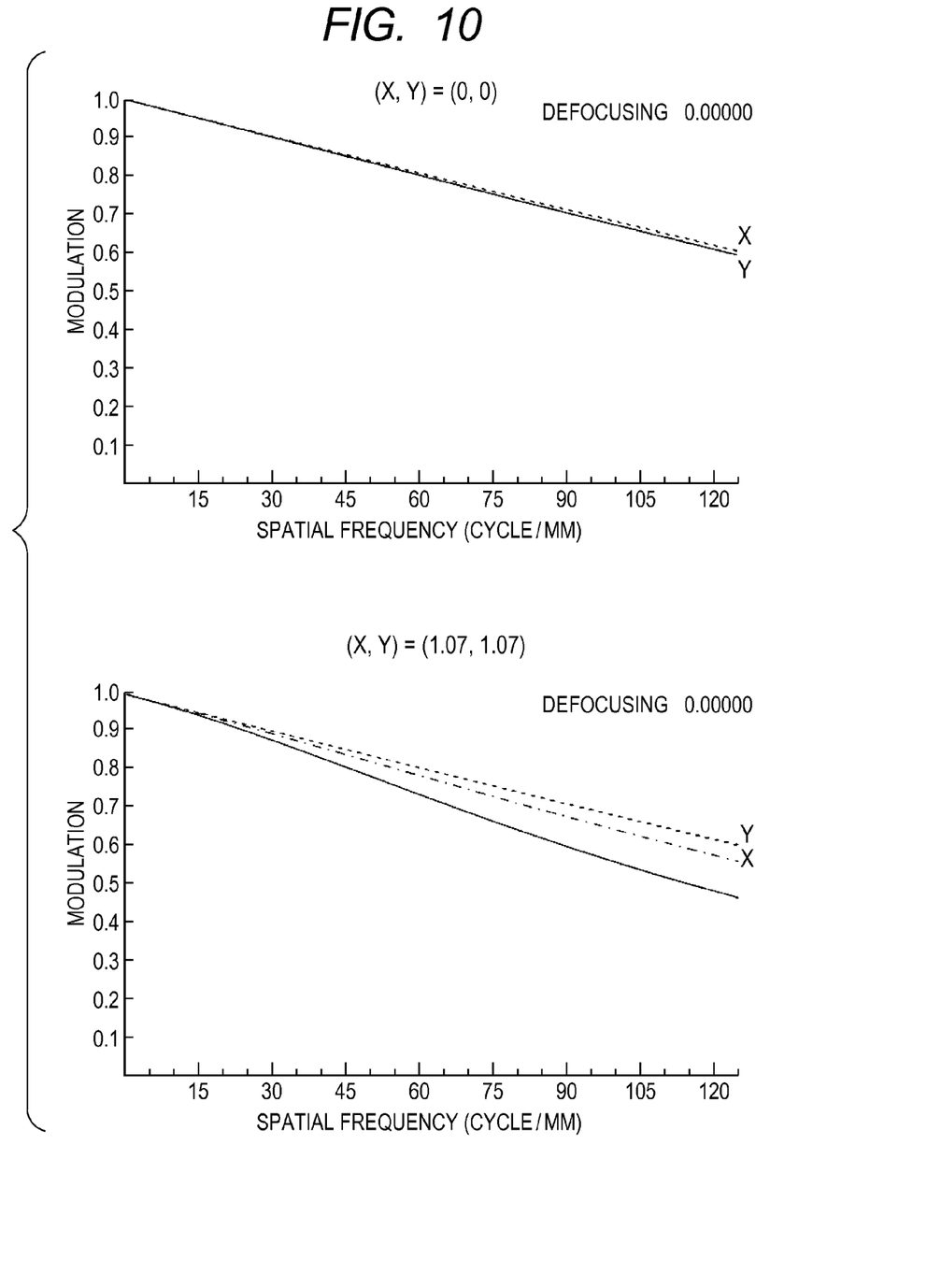
FIG. 10 is MTF diagrams of the optical system according to the third embodiment of the present invention.

In this case, the spherical mirrors 21 and 22 are disposed so that the x scanner 11 and the eyeball pupil 41 are optically conjugate to each other in the xz cross section. In addition, the cylindrical mirror 32 has optical power only in the yz cross sectional direction, and is disposed at the intermediate image position of the ocular optical system. Thus, the y scanner 12 and the eyeball pupil 41 are optically conjugate to each other also in the yz cross section without affecting the focused state. FIG. 10 illustrates MTF diagrams on the retina, and optical data is shown as follows. The units and the coordinate setting are the same as those in the case of the first embodiment.

| Surface No. | Radius curvature | X position | Y position | Z position | Rotational axis X | Rotational axis Y | Glass |
|---|---|---|---|---|---|---|---|
| Stop | ∞ | 0.000 | 0.000 | 0.000 | 0.000 | 0.000 | Air |
| 2 | ∞ | 0.000 | 0.000 | 30.000 | 45.000 | 0.000 | (Reflection) |
| 3 | ∞ | 0.000 | 0.000 | 30.000 | 90.000 | 0.000 | Air |
| 4 | ∞ | 0.000 | −8.000 | 30.000 | 90.000 | 45.000 | (Reflection) |
| 5 | ∞ | 0.000 | −8.000 | 30.000 | 0.000 | 90.000 | Air |
| 6 | −200.000 | −92.000 | −8.000 | 30.000 | −90.000 | 86.000 | (Reflection) |
| 7 | ∞ | −92.000 | −8.000 | 30.000 | −90.000 | 82.000 | Air |

-continued

| Surface No. | Radius curvature | X position | Y position | Z position | Rotational axis X | Rotational axis Y | Glass |
|---|---|---|---|---|---|---|---|
| 8 | 2500.000 | 7.027 | 5.917 | 30.000 | −90.000 | 88.000 | (Reflection) (CYL) |
| 9 | ∞ | 7.027 | 5.917 | 30.000 | 90.000 | 86.000 | Air |
| 10 | −400.000 | −192.486 | 19.869 | 30.000 | 90.000 | 89.000 | (Reflection) |
| 11 | ∞ | −192.486 | 19.869 | 30.000 | −90.000 | 88.000 | Air |
| 12 | ∞ | 7.392 | 26.849 | 30.000 | −90.000 | 88.000 | (Eyeball incident surface) |

The returning light from the lens surface, which is generated in the first embodiment using the cylindrical lens, is not generated in the case where the eccentric cylindrical mirror is used as in this embodiment. Therefore, it can be said that the use of the mirror as units for reducing the pupil position shift amount $\Delta Z_2$ for the surface having different powers in the cross sectional directions is advantageous in the instrument for inspecting the retina reflection light or the like.

Fourth Embodiment

Figure 11:
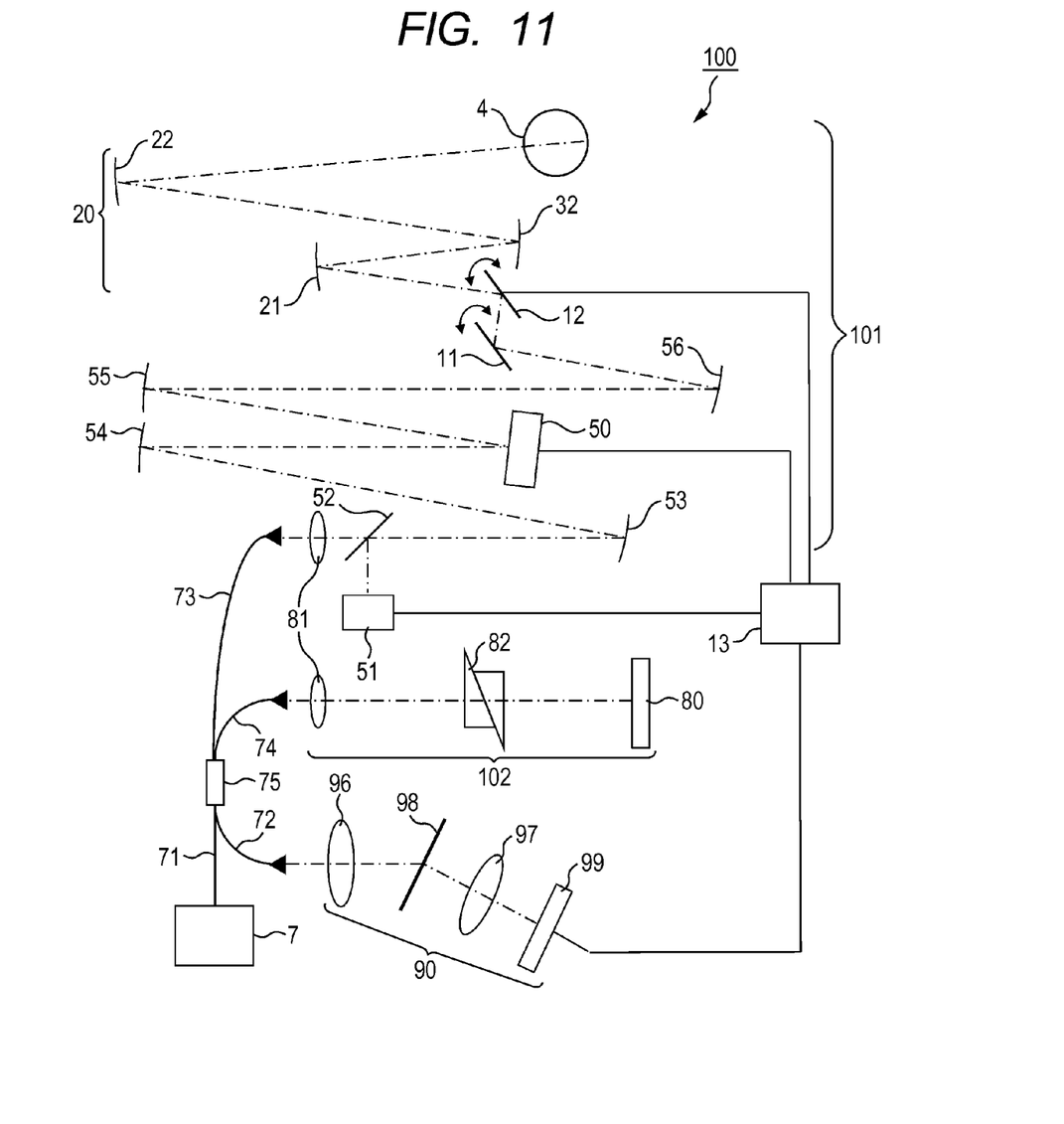
FIG. 11 is a structural diagram of an OCT according to a fourth embodiment of the present invention.

FIG. 11 illustrates a structure of the compensation optics OCT using an ocular optical system of this embodiment. This OCT 100 is a spectral domain (SD)-OCT including the light source 7, an observation arm 101, a reference arm 102, and a spectroscope 90. The ocular optical system 20 of the third embodiment is applied to the observation arm 101. As a matter of course, the ocular optical system of the first embodiment or second embodiment may be applied.

The beam emitted from the light source 7 propagates in a fiber 71 and is split by a fiber coupler 75 into fibers 73 and 74 at a predetermined ratio. The light that has propagated in the fiber 73 is emitted from an emission end on the observation arm side and is collimated by the collimator lens 81. Then, the light is sent to a reflection type wavefront compensator 50 via concave mirrors 53 and 54. In this case, the wavefront compensator 50 is the state of non-working flat surface. The reflected beam is reflected by concave mirrors 55 and 56, and enters the eyeball 4 via the scanners 11 and 12, and the ocular optical system 20. Here, the ocular optical system 20 is constituted of the spherical mirrors 21 and 22, and the cylindrical mirror 32. After that, the light is condensed to the retina by the anterior ocular segment optical system of the eyeball. Further, the reflected and scattering light propagates in the eyeball anterior ocular segment, the ocular optical system 20, the wavefront compensator 50, and the like along the incident optical path in the opposite direction, and then is split by a branching part 52 constituted of a beam splitter or the like at a predetermined ratio. Here, the reflected beam is detected by a Shack-Hartmann type wavefront sensor 51 so that wavefront aberration generated by the optical system of the eyeball 4 is measured. The measured wavefront aberration value is sent to a computer 13, in which a control value for the wavefront compensator 50 is calculated. After that, the wavefront compensator 50 is driven to cancel the aberration based on the control value. Here, the wavefront compensator 50 may be a variable shape mirror or a space optical modulator.

By the driven wavefront compensator 50, the wavefront of the illumination beam entering the eyeball has such characteristics that the aberration of the optical system of the eyeball is inverted. Therefore, the aberration is canceled and reduced in the eyeball, with the result that an image is formed on the retina in a good condensing state close to the diffraction limitation. On the other hand, the light reflected and scattered at the condensing point becomes a wavefront having aberration again when the light passes through the optical system of the eyeball 4. However, after propagating along the incident optical path in the opposite direction, the aberration is corrected by the wavefront compensator 50 in the same manner, and is connected appropriately to the fiber 73 via the collimator lens 81.

On the other hand, in the reference arm 102, the beam emitted from the end of the fiber 74 is collimated by the collimator lens 81 in the same manner, passes through a dispersion compensation glass 82, and is reflected by a turn back mirror 80. After that, the beam is connected to the fiber 74 again via the original optical path.

The individual beams that have propagated in the fibers 73 and 74 are combined by the coupler 75 and the combined beam propagates in the fiber 72 so as to be sent to the spectroscope 90. The light emitted from the fiber end is collimated by a lens 96 and is separated into individual wavelengths of light by a grating 98, which are then condensed on a one-dimensional sensor 99 by an imaging lens 97. The light intensities of the individual wavelengths detected by the sensor 99 are converted into electric signals and are sent to the computer 13. The signal is Fourier transformed after converting the wavelength into a wave number, so as to determine scattering intensity with respect to a position in the vertical direction. This is performed for each of the beam positions of scanning so that a tomographic image and a three-dimensional image are obtained. In this way, when the ocular optical system of the first, second, or third embodiment is used for the OCT, good performance can be obtained without increasing the entire size even if a thick beam is formed as the beam entering the pupil and the compensation optical system is disposed in the OCT. In other words, by using the ocular optical system of the first, second, or third embodiment for the OCT, a fundus image generating apparatus can be realized.

In this embodiment, the case where the ocular optical system is applied to the OCT is described, but needless to say, the same effect can be obtained even in the case where the ocular optical system is applied to the SLO.

Another Embodiment

In addition, the present invention can also be realized by performing the following process. Specifically, the process includes supplying software (program) that realizes the function of the embodiments described above to a system or an apparatus via a network or various storage media so that a computer (or CPU, MPU, or the like) of the system or the apparatus reads and executes the program.

REFERENCE SIGNS LIST

3 . . . cylindrical lens (second optical element)
6 . . . incident beam
7 . . . light source
11, 12 . . . one-dimensional scanner (one-dimensional scanning unit)
21 . . . lens unit (first optical element)
31 . . . cylindrical surface While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-094119, filed Apr. 15, 2010, which is hereby incorporated by reference herein in its entirety.

The invention claimed is:

1. An ophthalmologic apparatus, comprising:
two scanning units configured to scan a measuring light in directions different from each other in a fundus of an eye to be inspected, one of the two scanning units being disposed at a position that is optically conjugate to an anterior ocular segment of the eye to be inspected; and
an optical unit configured to have a surface having different optical powers corresponding to scan directions of the two scanning units so as to adjust optically a position of the other of the two scanning units to be optically conjugate to the anterior ocular segment of the eye to be inspected,
wherein the other of the two scanning units is disposed at a position that, without the optical unit being present, would not be optically conjugate to the anterior ocular segment, and
wherein the surface of the optical unit is disposed at a position that is optically conjugate to the fundus of the eye to be inspected.

2. The apparatus according to claim 1, wherein the surface has optical power corresponding to a scan direction of the other scanning unit of the two scanning units that is larger than optical power corresponding to a scan direction of the one scanning unit.

3. The apparatus according to claim 2, wherein the surface is curved in a direction corresponding to the scan direction of the other scanning unit such that the positions of the two scanning units are optically conjugate to the anterior ocular segment.

4. The apparatus according to claim 1, wherein the surface comprises a cylindrical surface having optical power in a direction corresponding to the scan direction of the other scanning unit, and
wherein the cylindrical surface is disposed at a position that is optically conjugate to the fundus of the eye.

5. The apparatus according to claim 4, wherein the optical unit comprises a second optical element having the cylindrical surface,
wherein a first optical element without the cylindrical surface is disposed between the two scanning units and the optical unit, and
wherein where $f_{21}$ represents a focal length of the first optical element, $s_{21}$ represents a distance between a principal point of the first optical element on the scanning unit side and a reference point of, out of the two scanning units, a scanning unit that scans the measurement light in a cross sectional direction in which the cylindrical surface has optical power, $s_3$ represents a distance between a principal point of the first optical element on the side of the eye to be inspected and a principal point of the second optical element on the scanning unit side, and $f_{CYL}$ represents a focal length of the second optical element, the following relational expression is satisfied:

$$f_{CYL} = -1/\{1/s_{21} + 1/f_{21}\} - s_3.$$

6. The apparatus according to claim 1, wherein in a case where a magnification of an optical system including the two scanning units is expressed by $\beta$=(a diameter of an incident light to the eye to be inspected)/(a diameter of an incident light to the two scanning units), $\beta>1$ is satisfied.

7. The apparatus according to claim 1, wherein a normal to the surface having the different optical powers corresponding to the two scan directions in an optical axis of an optical system including the two scanning units is inclined with respect to the optical axis of the optical system.

8. The apparatus according to claim 1, further comprising a compensation optical system between a light source and the two scanning units, the compensation optical system including a wavefront sensor for detecting a light wavefront and a wavefront compensator that is driven according to a wavefront aberration measured by the wavefront sensor.

9. The apparatus according to claim 1, further comprising an obtaining unit configured to obtain an image of the fundus of the eye based on reflection light obtained by scanning the fundus of the eye to be inspected by a measuring light emitted from a light source.

10. The apparatus according to claim 9, further comprising a light receiving unit configured to receive a combined light consisting of the reflection light and a reference light corresponding to the measuring light,
wherein the obtaining unit obtains a tomographic image of the fundus of the eye based on the combined light received by the light receiving unit as the image of the fundus of the eye.

11. A method of controlling the apparatus according to claim 1, the method comprising:
obtaining an image of the fundus of the eye based on reflection light obtained by scanning the fundus of the eye to be inspected by a measuring light emitted from a light source.

12. The method according to claim 11, further comprising receiving a combined light consisting of the reflection light and a reference light corresponding to the measuring light,
wherein the obtaining obtains a tomographic image of the fundus of the eye based on the received combined light as the image of the fundus of the eye.

13. The apparatus according to claim 1, wherein the optical unit comprises a cylindrical optical member.

14. The apparatus according to claim 1, wherein the optical unit comprises an anamorphic optical member.

15. The apparatus according to claim 1, wherein the optical unit is disposed at a position of an intermediate image in an optical system including the two scanning units.

16. The apparatus according to claim 1, wherein the optical unit is disposed at a position between a first lens group and a second lens group.

17. The apparatus according to claim 1, wherein the optical unit is disposed at a position between the anterior ocular segment of the eye and the two scanning units.

18. The apparatus according to claim 1, wherein the two scanning units are disposed close to each other.

19. An ophthalmologic apparatus, comprising:
an irradiating unit including two scanning units, one of the two scanning units being disposed at a position that is optically conjugate to an anterior ocular segment of an eye to be inspected, the irradiating unit being configured to irradiate a fundus of the eye to be inspected with a measuring light scanned by the two scanning units via the anterior ocular segment; and
an optical unit configured to have a surface having optical power corresponding to a scan direction of the other scanning unit of the two scanning units that is larger than optical power corresponding to a scan direction of the one scanning unit, so as to adjust optically a position of the other of the two scanning units to be optically conjugate to the anterior ocular segment, wherein the other of the two scanning units is disposed at a position that, without the optical unit being present, would not be optically conjugate to the anterior ocular segment, and wherein the surface of the optical unit is disposed at a position that is optically conjugate to the fundus of the eye to be inspected.

20. The apparatus according to claim 19, wherein one of the two scanning units is disposed at a position that is optically conjugate to the anterior ocular segment, and wherein the other of the two scanning units is disposed at a position that is adjacent to the one scanning unit and that, without the optical unit being present, would not be optically conjugate to the anterior ocular segment.

21. The apparatus according to claim 19, further comprising a compensation optical system between a light source and the two scanning units, the compensation optical system including a wavefront sensor for detecting a light wavefront and a wavefront compensator that is driven according to a wavefront aberration measured by the wavefront sensor.

22. The apparatus according to claim 19, further comprising an obtaining unit configured to obtain an image of the fundus of the eye based on reflection light obtained by scanning the fundus of the eye to be inspected by a measuring light emitted from a light source.

23. The apparatus according to claim 22, further comprising a light receiving unit configured to receive a combined light consisting of the reflection light and a reference light corresponding to the measuring light, wherein the obtaining unit obtains a tomographic image of the fundus of the eye based on the combined light received by the light receiving unit as the image of the fundus of the eye.

24. The apparatus according to claim 19, wherein the optical unit comprises a cylindrical optical member.

25. The apparatus according to claim 19, wherein the optical unit comprises an anamorphic optical member.

26. The apparatus according to claim 19, wherein the optical unit is disposed at a position of an intermediate image in an optical system including the two scanning units.

27. The apparatus according to claim 19, wherein the optical unit is disposed at a position between a first lens group and a second lens group.

28. The apparatus according to claim 19, wherein the optical unit is disposed at a position between the anterior ocular segment of the eye and the two scanning units.

29. A method of controlling the apparatus according to claim 19, the method comprising:

obtaining an image of the fundus of the eye based on reflection light obtained by scanning the fundus of the eye to be inspected by a measuring light emitted from a light source.

30. The method according to claim 29, further comprising receiving a combined light consisting of the reflection light and a reference light corresponding to the measuring light, wherein the obtaining obtains a tomographic image of the fundus of the eye based on the received combined light as the image of the fundus of the eye.

31. The apparatus according to claim 19, wherein the two scanning units are disposed close to each other.

* * * * *